(12) United States Patent  
Erdman et al.

(10) Patent No.: US 7,666,176 B2  
(45) Date of Patent: Feb. 23, 2010

(54) DISPOSABLE DIAPER WITH OPTIMAL LEAKAGE PROTECTION

(75) Inventors: Edward P. Erdman, West Chester, PA (US); Mariela Muniz, West Chester, PA (US)

(73) Assignee: First Quality Retail Services, LLC, Great Neck, NY (US)

( * ) Notice: Subject to any disclaimer, the term of this patent is extended or adjusted under 35 U.S.C. 154(b) by 0 days.

(21) Appl. No.: 11/524,762

(22) Filed: Sep. 21, 2006

(65) Prior Publication Data

US 2008/0077112 A1    Mar. 27, 2008

(51) Int. Cl.
*A61F 13/15* (2006.01)

(52) U.S. Cl. ............... 604/385.28; 604/385.25; 604/385.26; 604/385.29

(58) Field of Classification Search .......... 604/385.25, 604/385.26, 385.28, 385.29
See application file for complete search history.

(56) References Cited

U.S. PATENT DOCUMENTS

| 4,579,556 | A |   | 4/1986  | McFarland |
|-----------|---|---|---------|-----------|
| 4,892,528 | A |   | 1/1990  | Suzuki et al. |
| 5,147,345 | A | * | 9/1992  | Young et al. ............ 604/378 |
| 5,167,653 | A |   | 12/1992 | Igaue et al. |
| H1630     | H | * | 1/1997  | Roe et al. ............ 604/385.28 |

* cited by examiner

*Primary Examiner*—Jacqueline F. Stephens
(74) *Attorney, Agent, or Firm*—Amster, Rothstein & Ebenstein LLP

(57) ABSTRACT

The present invention provides for the improved prevention of leakage of body exudates from a disposable absorbent article, such as a diaper, by providing a pair of standing leg cuffs on both sides of the absorbent core of the article. The cuffs are preferably ribbon cuffs attached to the diaper or fashioned from the top sheet of the diaper.

8 Claims, 7 Drawing Sheets

DISPOSABLE DIAPER WITH OPTIMAL LEAKAGE PROTECTION

BACKGROUND OF THE INVENTION

The present invention relates generally to disposable absorbent articles. Specifically, the present invention relates to disposable absorbent articles designed for improved leakage protection.

Disposable absorbent articles such as disposable diapers, training pants, protective underwear, and the like are known. A typical disposable absorbent article frequently makes use of an absorbent core located between a top sheet and a back sheet. The top sheet is commonly formed of a material which is pervious to body fluids, e.g., urine, to allow the transfer of such fluids into the core. The back sheet is commonly formed of a liquid impervious material to provide a barrier wall so that fluid absorbed by the article cannot leak from the back sheet. The absorbent core is used to absorb the body exudates of the user wearing the article. Typically, fluff e.g., wood pulp or other cellulosic fiber, is used as the material of choice for the absorbent core.

In order to improve the absorbability of the absorbent core, highly absorptive polymers, sometimes referred to as "super-absorbent polymers" or "SAP" (which may be in the form of particles or fibers), are included with the fluff. However, the absorption rates of the absorbent core are not typically high enough to absorb a large quantity of liquids at a single time when such quantities are released onto the upper surfaces of the top sheet and the core. As a result, the liquid, at least partially, flows laterally onto the upper surface of the sheet and often leaks out along the side edges of the article. Such leakage occurs when the quantity of body fluid released is large.

In order to prevent such leakage, leakage-protecting baffles or cuffs are typically provided on the side edges of articles such as diapers. These cuffs contain a longitudinal elastic band. The cuffs secure the side edges of the diaper to the wearer's body, thereby preventing released body exudates from escaping from the diaper. However, in such designs, body exudates usually accumulate near the cuffs. Accordingly, there is always a possibility of the accumulated liquid leaking out from gaps formed between the cuffs and the body of the person wearing the diaper, for example when the wearer moves. Moreover, there is also a risk of liquid leaking out due to damage to the cuff U.S. Pat. No. 4,579,556 discloses a disposable diaper in which the opposite side edges of the absorbent core are covered with part of an impervious back sheet, thereby achieving a certain degree of leakage protection. However, there is a possibility of leakage of body exudates when the side edges are subjected to body pressures.

U.S. Pat. No. 4,892,528 discloses a disposable diaper in which two sheets, resistant to the passage of water, are disposed adjacent to and partially outward from two side surfaces of the absorbent core. The two sheets along with the back sheet are used to make leakage-protecting baffles, which extend above the top surface of the absorbent core. In this invention, there is a risk of released body exudate leaking out once such extended baffles twist due to body movement.

U.S. Pat. No. 5,167,653 discloses a disposable garment provided with a plurality of flaps extending along laterally opposite sides of the garment and normally biased by the elastic shrinking potential to turn upwards. The design of this invention makes the garment complicated and difficult to wear because of multiple flaps containing elastic members.

In light of the above described disadvantages, what is required is a disposable absorbent article that effectively prevents leakage. Additionally, the disposable absorbent article should prevent liquids from leaking irrespective of body movements or the posture of the person wearing the article.

SUMMARY

An improved disposable absorbent article comprises a liquid permeable top sheet, a liquid impermeable back sheet, a liquid absorptive core interposed between the top sheet and the back sheet, a first pair of standing leg ribbon cuffs located outwardly with respect to the core along laterally opposite sides, and a second pair of standing leg cuffs, located along laterally opposite sides of the core at a predefined distance from the first pair of cuffs. In one embodiment of the invention, the first pair of cuffs is fashioned from the top sheet of the garment.

The present invention provides an improvement in the mechanism for blocking the leakage of body exudates from a diaper by providing a pair of standing leg cuffs on both sides of the absorbent core of the diaper.

BRIEF DESCRIPTION OF THE DRAWINGS

These and other features and advantages of the present invention will be appreciated, as they become better understood by reference to the following Detailed Description when considered in connection with the accompanying drawings.

DETAILED DESCRIPTION OF THE INVENTION

In the present specification, specific embodiments of the present invention have been described. However, one of ordinary skill in the art will appreciate that various modifications and changes can be made without departing from the spirit and scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as critical, required, or essential features or elements of any or all of the claims.

With reference to the drawings, a new design for a disposable absorbent article is described with the principles and embodiments as set out below. The new design provides an improved mechanism for preventing the leakage of body exudates from a disposable absorbent article such as a diaper. In accordance with the novel design, a disposable absorbent article is provided with a second ribbon cuff in addition to the existing ribbon or non ribbon cuff in the absorbent article.

Figure 1:
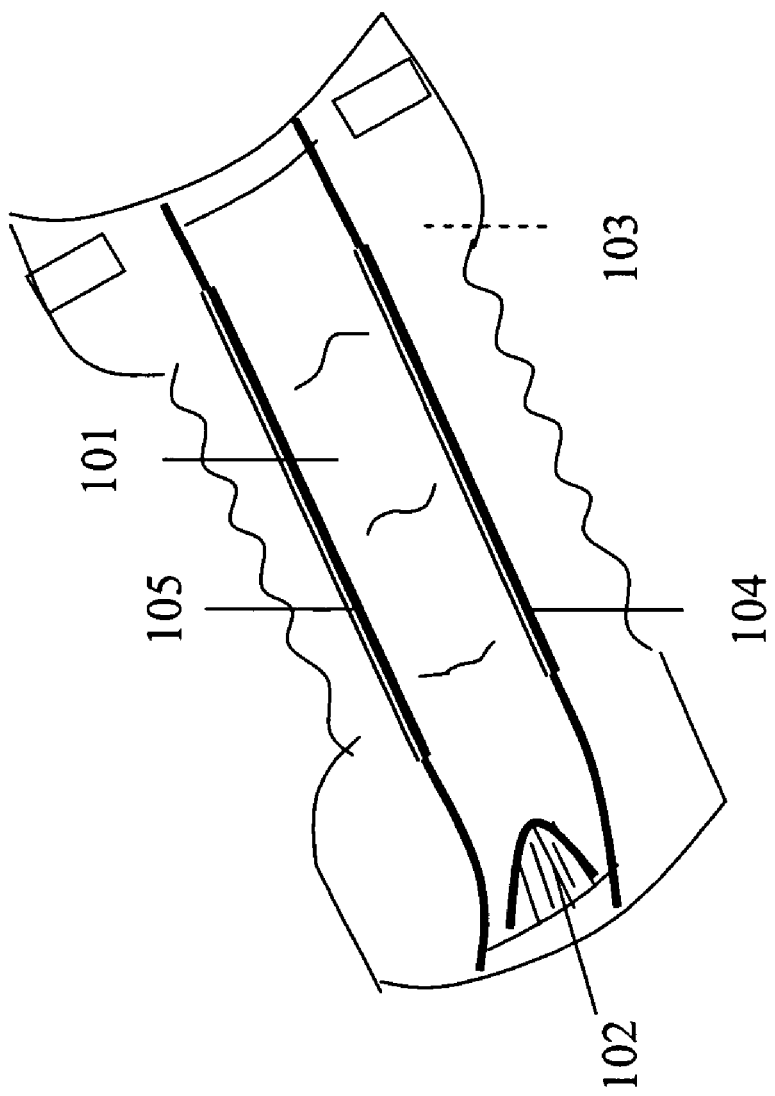
FIG. 1 is a schematic view of a diaper comprising a single cuff design for preventing leakage of body exudate from the diaper.

FIG. 1 shows a schematic view of a disposable article such as a diaper comprising a unitized standing single cuff utilized for preventing the leakage of body exudates from the diaper. It comprises top sheet 101, core 102, back sheet 103, and single cuffs 104 and 105. Top sheet 101 forms the upper surface of the diaper and contains apertures. Core 102 is fibrous and absorbs body exudates. Back sheet 103 forms the bottom surface of the diaper and is liquid impervious. Cuffs 104 and 105 are provided on the opposite sides of core 102 and are made of liquid impervious ribbons. Longitudinal elastic bands are provided within these cuffs.

The liquid released onto top sheet 101 of the diaper passes through the apertures down to core 102 that absorbs them. The unabsorbed liquids flow laterally onto top sheet 101 to the sides and reach cuffs 104 and 105. Cuffs 104 and 105 prevent liquids from flowing out of the diaper.

Figure 2:
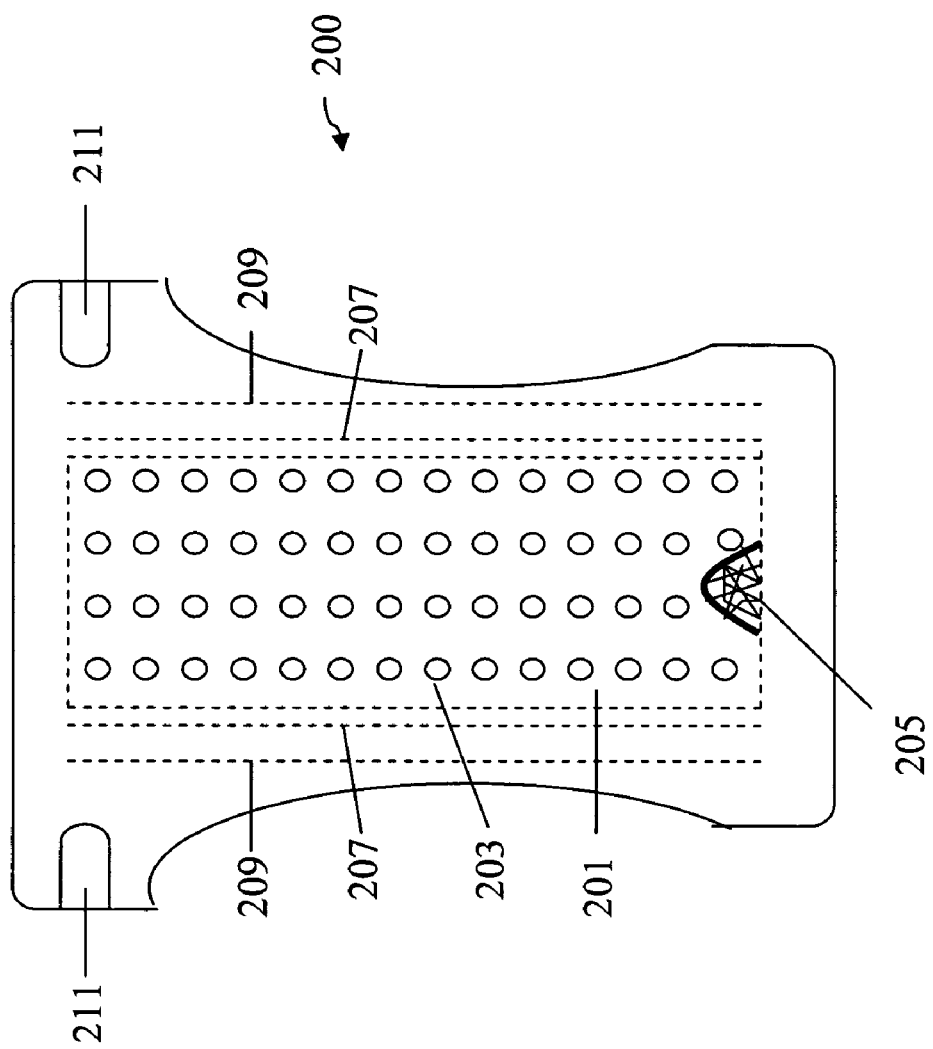
FIG. 2 is a top plan view of a diaper being unfolded in accordance with an embodiment of the present invention.

FIG. 2 shows a top plan view of an embodiment of a disposable absorbent article e.g., a diaper 200 constructed according to the present invention, being unfolded. Diaper 200 comprises top sheet 201, apertures 203, core 205, a first pair of cuffs 207, a second pair of cuffs 209, and tape fasteners 211. Top sheet 201 is liquid permeable and forms the top surface of the diaper. Top sheet 201 is provided with multiple apertures 203 on the surface there through. Excreted liquids pass through these apertures onto core 205. The pair of cuffs 207 and 209 are provided on two opposite sides of the absorbing core and extend longitudinally along the length of the diaper. Cuffs 207 and 209 prevent the outflow of body exudates from the diaper. Tape fasteners 211 are provided to fasten the diaper about the body of the wearer.

Figure 3:
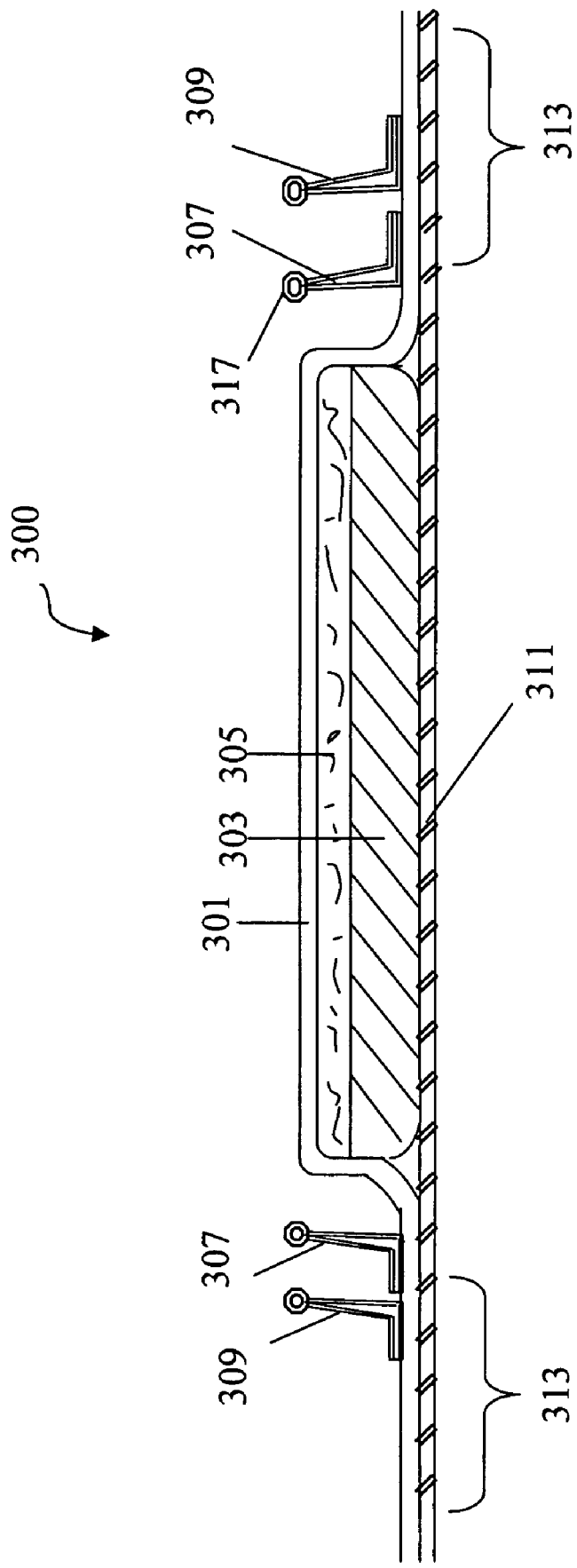
FIG. 3 is a cross-sectional view of a diaper in accordance with an embodiment of the present invention.

FIG. 3 shows a cross sectional view of a diaper 300 in accordance with an embodiment of the present invention. Diaper 300 comprises top sheet 301, absorbent core 303, isolating layer or acquisition layer 305, a pair of cuffs 307 and 309, back sheet 311, and a pair of laterally opposite base flaps 313. Base flaps 313 are formed of portions of top sheet 301 and back sheet 311 bonded together by adhesive bonding or welding. Excreted liquids pass through apertures in top sheet 301 to isolating layer 305 and finally to absorbent core 303. Isolating layer 305 is disposed between the topsheet 301 and absorbent core 303, isolating both from each other and allowing body exudates to pass rapidly there through. Isolating layer 305 reduces the possibility that body exudates, which have been absorbed by the absorbent core 303, flow again to the top surface of absorbent core 303 and leak through top sheet 301. The body exudate is absorbed by absorbent core 303. However, absorbent core 303 may not be able to retain all the body exudate and some liquid might leak from absorbent core 303. This liquid flows laterally towards the sides of absorbent core 303. The liquid migrates from absorbent core 303 and moves towards the edges of diaper 300. A first pair of cuffs 307 is provided on both sides of absorbent core 303, preventing the leakage of liquid. In case some liquid manages to pass through or over the first pair of cuffs 307, a second pair of cuffs 309 is provided to prevent any further leakage.

Both cuffs 307 and 309 are ribbon standing leg cuffs and are attached to base flaps 313 by adhesive bonding or welding. Cuffs 307 and 309 run along the side edge of the core of the diaper, and project above the upper surface of absorbent core 303. Each cuff is formed from a narrow folded-over nonwoven material to form a unitized cuff structure. The nonwoven that makes up the cuff can be made from liquid impervious material. A longitudinal elastic band 317 is interposed at or near the fold-over point of the nonwoven material. Cuffs 307 and 309 are maintained in an upright position under a tensile force due to the contractibility of elastic band 317 contained therein, which tends to raise the respective cuffs into a bow shape. When the diaper is placed on the wearer, the cuffs are caused to laterally expand, thus forming a desirable snug fitting area having extended dimensions and elastic tension.

Figure 4:
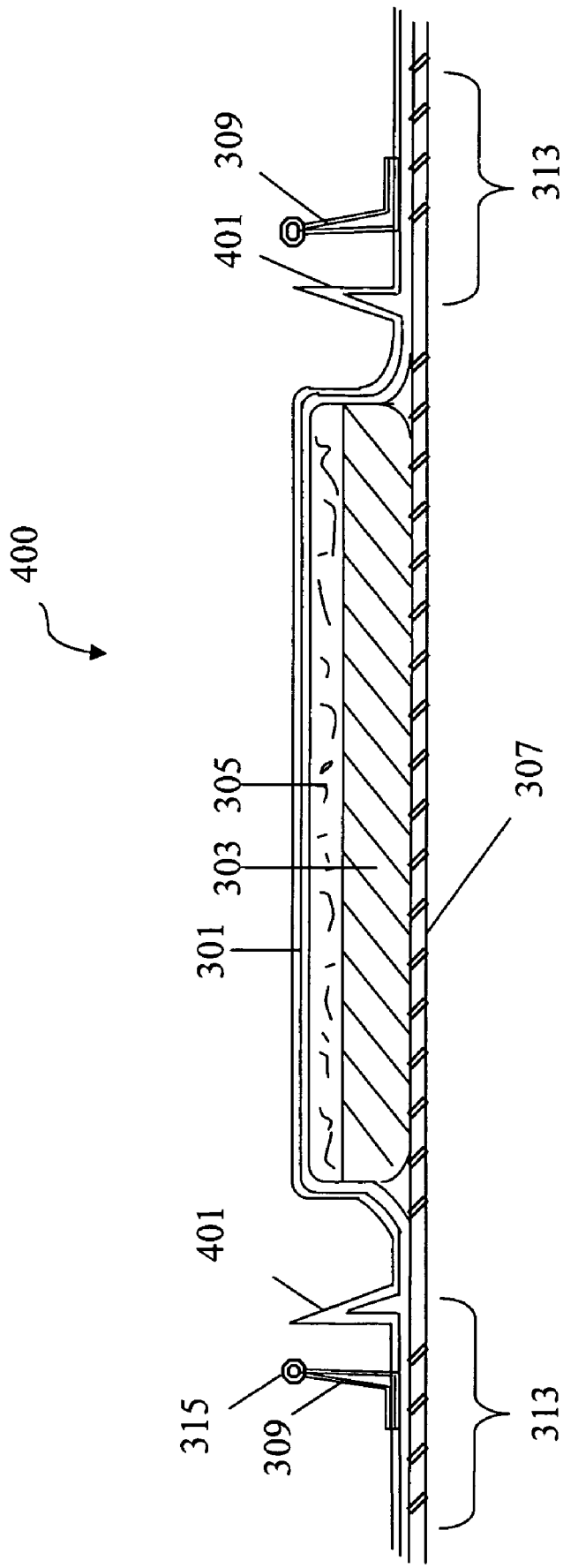
FIG. 4 is a cross-sectional view of a diaper in accordance with an alternate embodiment of the present invention where a first pair of cuffs is fashioned from the top sheet and a second pair is ribbon cuffs.

FIG. 4 is a cross-sectional view of a diaper 400 in accordance with another embodiment of the invention. A first pair of cuffs 401 in diaper 400 are fashioned from top sheet 301, while a second pair of cuffs 309 are ribbon cuffs attached to base flaps 313 by adhesive or welding. The fashioning of a first pair of cuffs 401 from top sheet 301 may be achieved by mechanically folding the material of top sheet 301, thus requiring only a single material feed.

Figure 5:
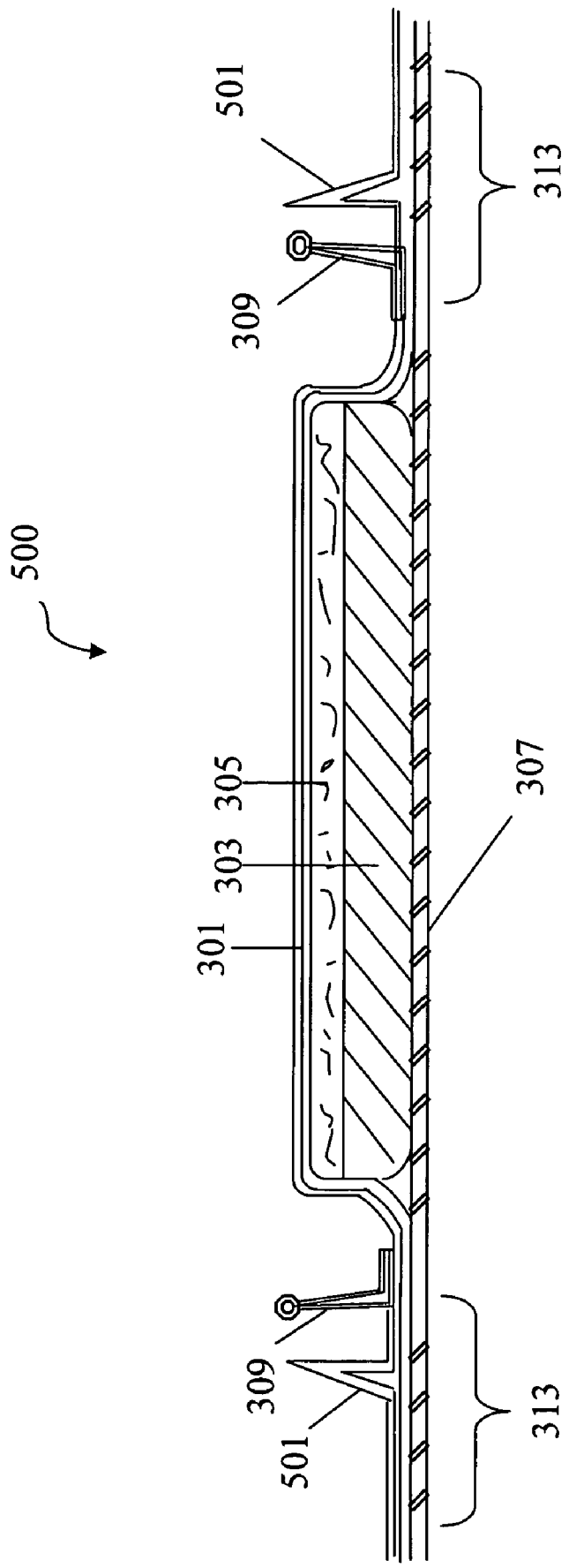
FIG. 5 is a cross-sectional view of a diaper in accordance with an alternate view of the invention where a first pair of cuffs is ribboned cuffs and a second pair of cuffs is fashioned from the top sheet.
Figure 6:
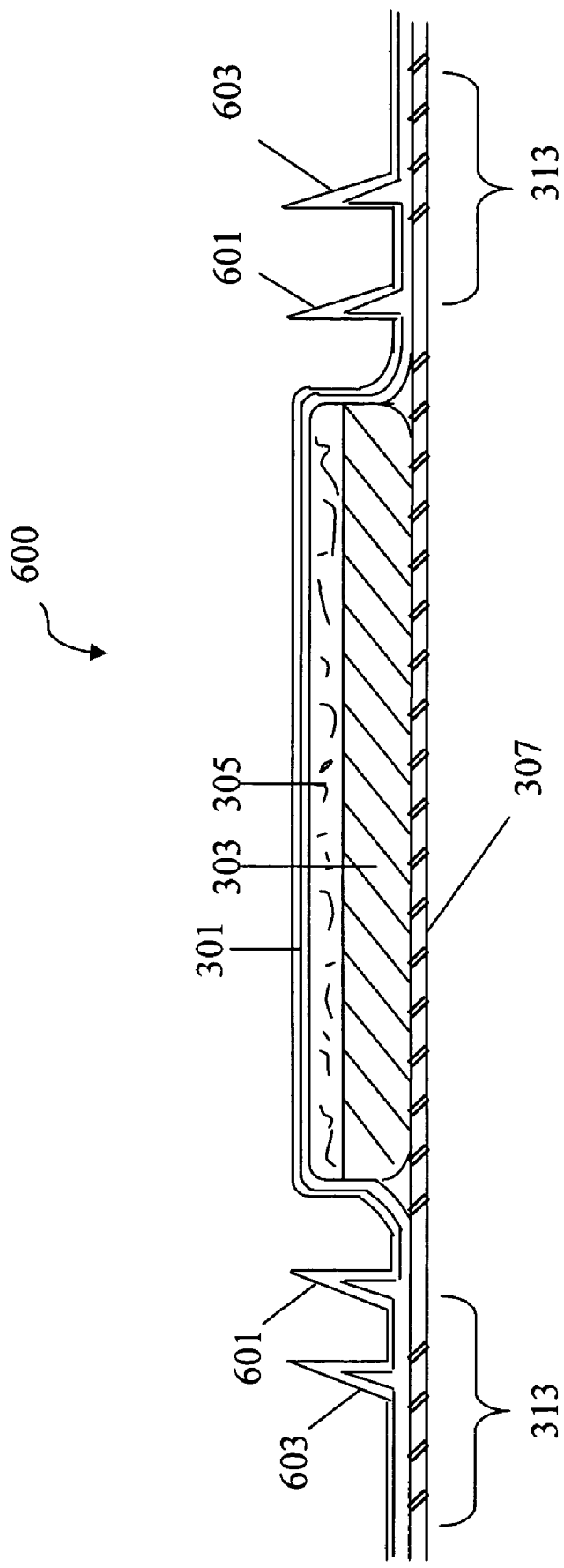
FIG. 6 is a cross-sectional view of a diaper in accordance with an alternate embodiment of the invention where both a first pair of cuffs and a second pair of cuffs is fashioned from the top sheet.

FIG. 5 is an alternate embodiment showing diaper 500 where a first pair of cuffs 309 are ribbon cuffs while a second pair of cuffs 501 are fashioned from the top sheet. It will be obvious to one skilled in the art that in another embodiment both the first pair and the second pair of cuffs may be fashioned from top sheet 301. FIG. 6 is an embodiment showing diaper 600 where both pair of cuffs 601 and 603 are made from top sheet 301.

Referring to FIGS. 3 to 6, top sheet 301 is formed from a material such as a fibrous non-woven fabric or porous plastic film. Preferred non-woven materials include spun-bonded polypropylene, spun-bonded polyethylene, and thermally bonded webs of staple fibers. Back sheet 311 is are made from a material such as a plastic film or laminate sheet of plastic film. The plastic film is preferably air-impermeable. Such material should be hydrophobic, soft in texture, and strong in tensile strength. An example includes hydro-entangled non-woven webs, which may contain some cotton and/or rayon fibers blended in with thermal-plastic fibers. Cellulose fibers can also be blended in at small percentages to reduce cost. Other materials for forming the back sheet may include polypropylene films, co-extruded films (polyethylene and ethylene vinyl acetate), co-polymer films (polyethylene/polypropylene), and polylaminates (polypropylene nonwoven and polyethylene film). Absorbent core 303 can be made up of any suitable absorbent material, as well as combinations of different types of absorbent materials. For example, the absorbent core may be formed of a mixture of pulp fluff and super absorbent polymer particles wrapped in a liquid permeable tissue wrap. The super absorbent polymer particles may be substantially homogeneously mixed with the hydrophilic fibers, or may be non-uniformly mixed. The pulp fluff may be exchanged with synthetic, polymeric, meltblown fibers, or with a combination of meltblown fibers and natural fibers. Examples of super absorbent polymer materials include polyacrylamides, polyvinyl alcohol, polyacrylates, various grafted starches, and the like. A desired super absorbent material is a cross-linked polysodium acrylate, which can be purchased from BASF Corporation of Portsmouth, Va., under the trademark ASAP 2260. Absorbent core 303 may be bonded to the top sheet 301 and back sheet 311 with adhesives or welding. Elastic bands 317 comprise material such as thread- or tape-like rubber, tape-like plastic foam or plastic film.

Figure 7:
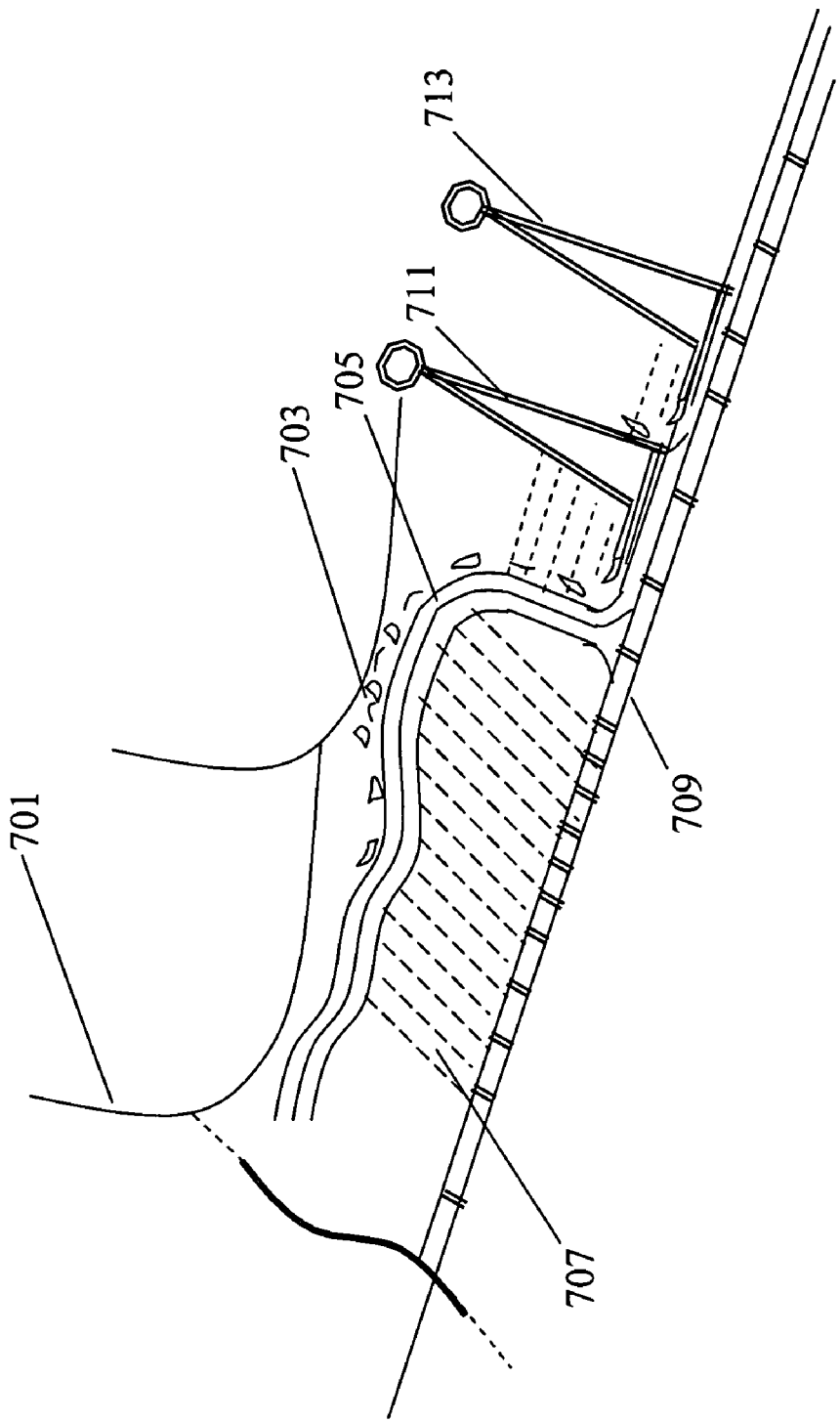
FIG. 7 is a partial cross-sectional view of a diaper in accordance with an alternate embodiment of the invention depicting cuffs preventing body exudates from leaking out of the diaper.

FIG. 7 is a partial cross-sectional view of a diaper of the present invention depicting the pair of cuffs preventing body exudates from leaking. FIG. 7 shows a user 701, body exudates 703, top sheet 705, absorbent core 707, back sheet 709, and cuffs 711 and 713. User 701 discharges liquids 703 on top sheet 705, which passes through the apertures (not shown) into absorbent core 707. Absorbent core 707 absorbs a major quantity of liquid 703. However, some body exudates 703 remain on the topsheet 705, or may seep back from absorbent core 707 to top sheet 705. Cuff 711, projecting above the surface of top sheet 705, prevents most if not all of the liquid from reaching the edge of diaper. The top end of cuff 711 is in contact with the body of user 701. This cuff arrangement prevents the liquid from leaking out of the diaper.

Having described the invention, it is readily apparent that various modifications can be made to the above constructions without departing from the scope of the invention. Therefore, it is intended that all the matter contained in the above description should be interpreted as illustrative and not in a limiting sense. The present invention can be used in other contexts, such as in other garments to retain liquids.

What is claimed is:

1. A disposable absorbent article comprising:
a liquid permeable top sheet;
a liquid impermeable back sheet;
an absorbent core interposed between the top sheet and the back sheet;
a first pair of liquid impermeable standing leg ribbon cuffs disposed outwardly from the absorbent core along laterally opposite sides thereof;
a second pair of liquid impermeable standing leg ribbon cuffs disposed along laterally opposite sides of the absorbent core at a predetermined distance from the first pair of cuffs, said second pair of cuffs disposed outwardly from the first pair of cuffs such that said first pair of cuffs is positioned between the absorbent core and the second pair of cuffs; and
wherein each of the first and second pairs of cuffs are disposed outwardly from the absorbent core on laterally opposite sides thereof so as not to overlap the absorbent core.

2. The disposable absorbent article of claim 1, wherein the standing leg ribbon cuffs are formed from separate ribbons containing an elastic band.

3. A disposable absorbent article comprising:
a liquid permeable top sheet;
a liquid impermeable back sheet;
an absorbent core interposed between the top sheet and the back sheet;
a first pair of cuffs disposed outwardly from the core along laterally opposite sides thereof, wherein the first pair of cuffs is fashioned from the top sheet;
a second pair of liquid impermeable cuffs having their base edges disposed at a predetermined distance from the base edges of the first pair of cuffs, said second pair of cuffs disposed outwardly from said first pair of cuffs such that the first pair of cuffs is positioned between the absorbent core and the second pair of cuffs; and
wherein each of the first and second pairs of cuffs are disposed outwardly from the absorbent core on laterally opposite sides thereof so as not to overlap the absorbent core.

4. The disposable article of claim 3, wherein the second pair of cuffs are ribbon standing leg cuffs.

5. The disposable article of claim 3, wherein the absorbent core comprises an isolating layer.

6. The disposable article of claim 5, wherein the isolating layer separates the absorbent core from the top sheet and prevents the liquids absorbed by the absorbent core from flowing back to the top sheet.

7. The disposable article of claim 3, wherein the disposable garment is a diaper.

8. The disposable article of claim 3, wherein the disposable garment is a training pant.

* * * * *